US00PP20009P2

(12) United States Plant Patent
Korlipara

(10) Patent No.: US PP20,009 P2
(45) Date of Patent: May 19, 2009

(54) *COREOPSIS* PLANT NAMED 'MOONLIGHT'

(50) Latin Name: *Coreopsis*
Varietal Denomination: Moonlight

(75) Inventor: Harini Korlipara, Canby, OR (US)

(73) Assignee: Terra Nova Nurseries, Inc., Canby, OR (US)

( * ) Notice: Subject to any disclaimer, the term of this patent is extended or adjusted under 35 U.S.C. 154(b) by 0 days.

(21) Appl. No.: 12/156,829

(22) Filed: Jun. 3, 2008

(51) Int. Cl.
*A01H 5/00* (2006.01)

(52) U.S. Cl. ..... Plt./417

(58) Field of Classification Search ..... Plt./417
See application file for complete search history.

*Primary Examiner*—Annette H Para
(74) *Attorney, Agent, or Firm*—Klarquist Sparkman, LLP

(57) ABSTRACT

A new and distinct *Coreopsis* plant named 'Moonlight' characterized by prolific, large, light yellow daisy-type flowers, grass-green foliage, very free branching and flowering, long bloom time, and a mounding habit.

1 Drawing Sheet

Botanical denomination: *Coreopsis* spp.
Variety designation: 'Moonlight'.
Cross reference to *Coreopsis* 'Autumn Blush' (U.S. Plant patent application No. 11/452,687, now U.S. Plant Pat. No. 18,184).

BACKGROUND OF THE INVENTION

The present invention relates to a new and distinct hybrid of *Coreopsis* and given the cultivar name 'Moonlight'. *Coreopsis* is in the family *Asteraceae*. This new cultivar originated from a branch mutation from *Coreopsis* 'Autumn Blush' found in a green house.

SUMMARY OF THE INVENTION

The following traits have been repeatedly observed and are determined to be the unique characteristics of the new variety. These characteristics in combination distinguish *Coreopsis* 'Moonlight' as a new and distinct cultivar:

1. large daisy-type flowers that grow to 4 cm in diameter,
2. unique light yellow flowers that turn soft peach shades in cool weather,
3. grass-green foliage,
4. very free branching,
5. very free flowering,
6. long bloom time, and
7. mounding habit.

This new cultivar has been reproduced only by asexual propagation (cuttings and tissue culture). Each of the progeny exhibits identical characteristics to the original plant. Asexual propagation by cuttings and tissue culture using standard micropropagation techniques with terminal and lateral shoots, as done in Canby, Oreg., on shows that the foregoing characteristics and distinctions come true to form and are established and transmitted through succeeding propagations. The present invention has not been evaluated under all possible environmental conditions. The phenotype may vary with variations in environment without a change in the genotype of the plant.

BRIEF DESCRIPTION OF THE PHOTOGRAPH

The photograph shows a nine month old *Coreopsis* 'Moonlight' growing in the ground in the trial field in August in Canby, Oreg.

DETAILED PLANT DESCRIPTION

The following is a detailed description of the new *Coreopsis* cultivar based on observations of a nine-month-old specimen growing in the ground in full sun under typical outdoor conditions in the trial fields in August in Canby, Oreg. Canby is Zone 8 on the USDA Hardiness map. Temperatures range from a high of 95 degrees F. in August to 32 degrees F. in January. Normal rainfall in Canby is 42.8 inches per year. The color descriptions are all based on The Royal Horticultural Society Colour Chart.

Plant:
- *Type.*—Herbaceous perennial.
- *Hardiness.*—USDA Zones 7 to 9.
- *Size.*—45 cm wide and 30 cm tall to top of inflorescences.
- *Form.*—Mound.
- *Vigor.*—Excellent.
- *Roots.*—Fibrous, Grey Brown 199D, stems root easily from stem tip cuttings.

Stem:
- *Type.*—Ascending.
- *Size.*—22 cm tall and 3 mm wide.
- *Internode length.*—2 cm to 5 cm.
- *Surface.*—Glabrous.
- *Color.*—Green 137A.

Leaf:
- *Type.*—Simple.
- *Shape.*—Linear to pinnately lobed with a linear basal side lobe.
- *Arrangement.*—Opposite.
- *Length including petiole.*—Grows to 6 cm.
- *Width.*—Usually 3 mm, grows to 6 mm.
- *Margins.*—Entire.

*Apex.*—Acute.

*Base.*—Attenuate, clasping.

*Surface texture.*—Glabrous.

*Venation.*—Pinnate.

*Color.*—Top side — Green 137A. Bottom — Green 137B.

Inflorescence:

*Type.*—Long stalked terminal heads of daisy type inflorescences.

*Peduncle.*—10 cm to 14 cm tall, 1 mm wide, glabrous, Green 137B.

*Size.*—Grows to 4 cm wide and 10 mm deep.

*Immature.*—Round shape, 7 mm wide and 7 mm deep, top half Greyed Orange. 163C with the tip Greyed Purple 187A, the bottom half is Yellow Green 148A.

*Receptacle.*—Bowl shaped, 8 mm wide and 6 mm deep, Green 137A.

*Phyllary.*—In two series, stellate; inner series 8 lobes, each grows to 20 mm wide and 7 mm deep, lobes reflex, ovate, entire, acute, 9 mm long and 4.5 mm wide, both sides glabrous and colored on top half Yellow 13A sometimes tipped with Greyed Purple 187A, bottom half Yellow Green 147A; outer series with 8 lobes, each grows to 1.5 mm wide and 4 mm long, glabrous, lobes ovate, entire, acute, Green 137A on both sides.

*Lastingness.*—Each inflorescence lasts about 7 to 10 days.

*Bloom period.*—June through September in Canby, Oreg.

*Fragrance.*—Light, Chrysanthemum-like.

Florets:

*Type.*—Composite.

*Ray florets.*—8 with no stamen or pistil, obovate with the tip usually three lobed with lobes obtuse and notched and the central lobe the longest, entire, grows to 19 mm long, 10 mm wide, glabrous on both surfaces, claw 1.5 mm long; Color topside Yellow 4C in summer, in spring and fall with the cool nights the color changes to Greyed Orange 174C with a yellow base, Yellow Orange 14B; bottom side Yellow 4B in summer, in spring and fall, Greyed Orange 104 A on top half blending to Yellow Orange 14B on bottom half.

*Disc.*—Conic, deeper with maturity, 11 mm wide and becoming 4 mm deep with maturity, Greyed Yellow 161B when in bud, opening to Yellow Orange 17A.

*Disc florets.*—About 100 in number, 5 mm long and 1 mm wide, corolla 4 mm long, tubular, 4 lobed, lobes entire, acute, Yellow Orange 17A, tube Yellow 11B.

*Pistil.*—1, 6 cm long, ovary 1 mm long, Green White 157A, style 5 mm long, extruding, with 2-branched stigma, stigma Yellow Orange 17A and style Yellow 4A.

*Stamen.*—5, 3.5 mm long, filaments 1 mm long, Yellow 10A, anthers 1.5 mm long, Black 202A, pollen Yellow 10A.

Seed: none produced

*Fertility.*—Infertile.

Disease and pests: *Coreopsis* are susceptible to mildew and fungal spots. No resistance is known for this variety.

COMPARISONS TO SIMILAR *COREOPSIS*

Compared to *Coreopsis* 'Autumn Blush' (U.S. Plant Pat. No. 18,184), the mother plant, the new cultivar has inflorescences that are lighter in color with no distinctive maroon eye and has a light peach blush in the spring and fall rather than a pink blush.

Compared to *Coreopsis,* 'Snowberry' (U.S. Plant Pat. No. 18,560), the new variety does not have the distinctive maroon eye. The new variety has a cool temperature triggered blush of light peach which *Coreopsis* 'Snowberry' does not.

I claim:

1. A new and distinct *Coreopsis* plant as herein illustrated and described.

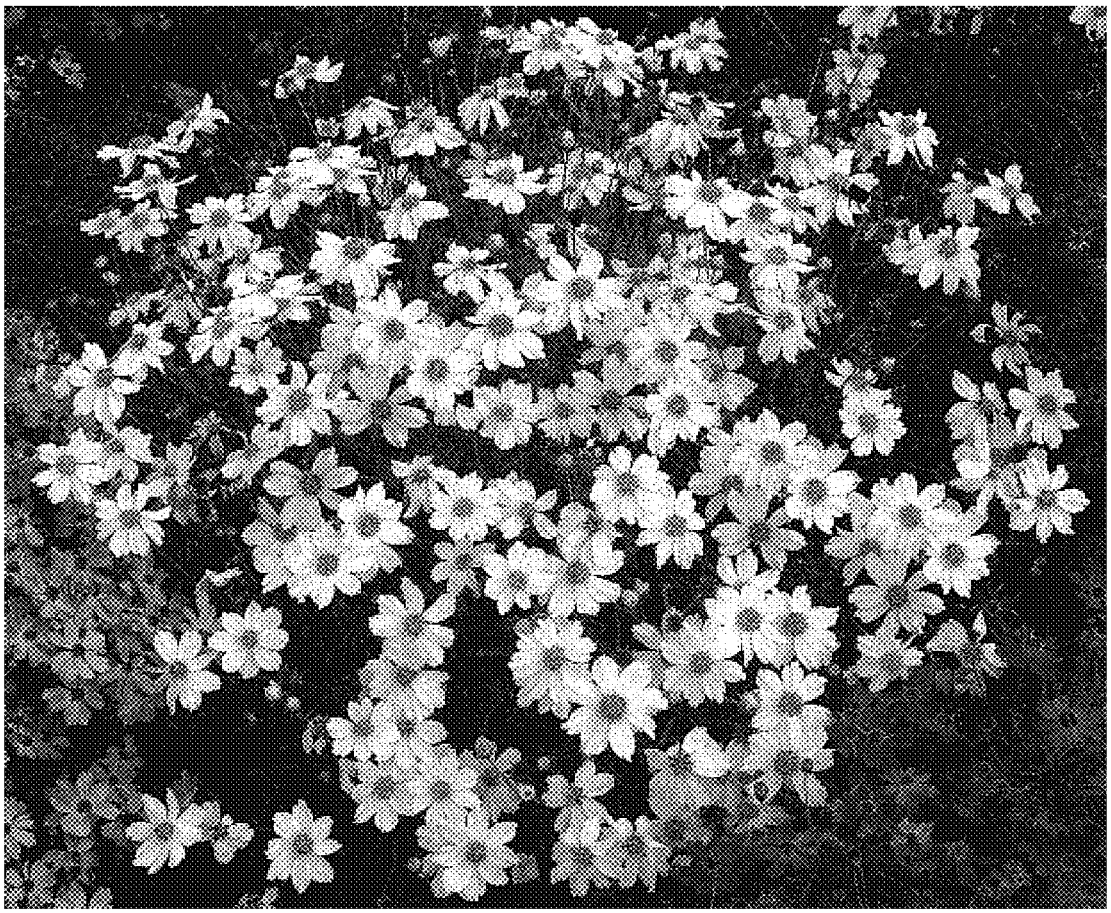

* * * * *